(12) United States Patent
Jones et al.

(10) Patent No.: US 7,168,597 B1
(45) Date of Patent: Jan. 30, 2007

(54) AEROSOL METERING VALVE

(75) Inventors: Anthony Patrick Jones, Ware (GB); Gregor John McLennan Anderson, Ware (GB); Paul Kenneth Rand, Ware (GB)

(73) Assignee: Smithkline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/936,505

(22) PCT Filed: Feb. 23, 2000

(86) PCT No.: PCT/EP00/01446

§ 371 (c)(1),
(2), (4) Date: Oct. 16, 2001

(87) PCT Pub. No.: WO00/55072

PCT Pub. Date: Sep. 21, 2000

(30) Foreign Application Priority Data

Mar. 12, 1999 (GB) ............................................. 9905568
Aug. 5, 1999 (GB) ............................................. 9918388

(51) Int. Cl.
*B65D 83/06* (2006.01)

(52) U.S. Cl. ............... 222/402.2; 222/450; 128/200.23; 604/186; 604/407; 251/65

(58) Field of Classification Search ............. 222/402.2, 222/402.24, 406, 407, 425, 434, 450; 251/65; 128/200.23; 604/186, 407
See application file for complete search history.

(56) References Cited

U.S. PATENT DOCUMENTS

| | | | |
|---|---|---|---|
| 3,402,861 A | 9/1968 | Cotes | |
| 3,666,144 A | 5/1972 | Winder | |
| 3,835,659 A | 9/1974 | McBride | |
| 3,848,775 A | 11/1974 | Possell | |
| 3,929,282 A | 12/1975 | Doll | |
| 3,974,941 A | 8/1976 | Mettler | |
| 4,061,251 A | 12/1977 | Harris | |
| 4,581,942 A | 4/1986 | Ogura | |
| 5,005,738 A | 4/1991 | Tempelman | |
| 5,085,351 A | * 2/1992 | Martin | ..................... 222/402.2 |
| 5,263,643 A | 11/1993 | Wells | |
| 5,353,828 A | 10/1994 | Troscinski | |
| 5,520,166 A | 5/1996 | Ritson | |
| 5,608,647 A | 3/1997 | Rubsamen | |
| 5,655,523 A | 8/1997 | Hodson | |
| 5,791,520 A | 8/1998 | Tichenor | |
| 5,873,361 A | 2/1999 | Hakala | |

FOREIGN PATENT DOCUMENTS

| | | |
|---|---|---|
| EP | 0 536 978 A | 4/1993 |
| EP | 567 348 A1 | 10/1993 |
| FR | 2 140 341 A | 1/1973 |
| FR | 2 730 219 A | 8/1996 |
| GB | 957 294 A | 5/1964 |
| GB | 2 085 553 A | 4/1982 |
| WO | WO 92 12750 A | 8/1992 |
| WO | WO 96 28367 | 9/1996 |
| WO | WO 96 32344 A | 10/1996 |
| WO | WO 96 32345 A | 10/1996 |
| WO | WO 99 15820 A | 4/1999 |
| WO | WO 00/53247 | 9/2000 |

* cited by examiner

*Primary Examiner*—Gene Mancene
*Assistant Examiner*—Patrick Buechner
(74) *Attorney, Agent, or Firm*—J. Michael Strickland

(57) ABSTRACT

A metering valve that includes a valve body defining a metering chamber having an inlet valve adapted to be reversibly actuable from an open position to a closed position located at the inlet, and an outlet valve adapted to be reversibly actuable from a dispensing to a non-dispensing position located at the outlet, where the outlet valve includes an outlet valve seat adapted to be in biasable contact with an outlet valve poppet is described. Aerosol containers and inhalation devices that include such metering valves are also described, as are methods of using such inhalation devices.

67 Claims, 14 Drawing Sheets

AEROSOL METERING VALVE

This invention relates to a metering valve for an aerosol container. The valve is particularly suitable for use in the metered dispensing of medicament by way of an inhalation device.

It is known to dispense medicament in aerosol form from a metered dose inhalation de vice. Such devices commonly comprise a housing and supported therein, a container for the aerosol formulation. The container has a metering valve which generally is a slide or rotary valve. The slide or rotary valve comprises a valve stem which is movable against a restraining, generally frictional, force within a valve body from a dispensing position to a non-dispensing position.

In more detail, a slide valve typically comprises a valve body and with in the valve body a sealing ring. A valve stem having a dispensing passage therein is frictionally received by the sealing ring. The valve stem is slidably movable within the sealing ring from a valve-closed position to a valve-open position in which the interior of the valve body is in communication with the dispensing passage. An illustrative slide valve is described in PCT application no. WO96/28367.

Actuation of a slide valve involves the application of sufficient mechanical force to overcome the frictional force between the valve stem and the sealing ring. In currently marketed inhalation devices the mechanical force required to actuate the slide valve is generally of the order of 20–40N. This force is often supplied by the patient manually depressing the container and valve body attached thereto relative to the housing and valve stem supported thereby. The movement of the valve body relative to the valve stem results in actuation of the valve and hence release of medicament.

With some current inhalation devices having a slide or rotary valve the valve stem sometimes tends to stick, pause, or drag during the actuation cycle with the result that the patient can in some circumstances perceive a resistance as the valve stem is moved. This may be partly caused by medicament sedimenting or precipitating out of the aerosol formulation and depositing on the internal valve components, the presence of medicament on the sliding interface increasing the frictional force between the valve stem and the frictional seal. Various solutions to the problem of valve resistance have been suggested including the use of lubricant on the valve stem and the seal.

It may be understood that effective delivery of medicament to the patient using an inhalation device as described above is to an extent dependent on the patient's ability to coordinate the actuation of the device (e.g. firing of the aerosol) with the taking of a sufficiently strong inward breath. The required coordination can present difficulties to some patients, with the risk that these patients do not receive the appropriate dose of medicament. There have thus, been efforts to develop inhalation devices which do not rely on manual actuation by the patient, in particular those which are actuable in response to the breath of a patient. These devices are often known as breath-actuable devices.

Breath-actuable devices typically comprise a source of stored energy which on release actuates the slide valve of the medicament container and hence releases medicament, and a breath trigger which triggers the release of the stored energy in response to the breath of the patient. The stored energy source is required because the force required to actuate the slide valve (e.g. 20–40N as mentioned above) is too great to be suppliable by the patients breath alone. Illustrative breath-actuable devices are described in U.S. Pat. No. 5,655,523.

The applicants have now developed a metering valve which may be actuated without any need for a dispensing stem or other dispensing member to be moved relative to a valve body. Since the new valve requires no relative movement of a valve stem to the valve body the problem of resistance associated with some slide and rotary valves is eliminated.

The newly developed metering valve is furthermore, operable by the application of a significantly lower force than is required to operate a conventional metering valve having a slide or rotary valve. The force required can indeed, be so low that the valve is actuable by the force of a patient's breath alone. The present metering valve is thus, particularly suitable for use in breath-activated devices. Such devices can be much simpler than current breath-actuated devices because they do not necessarily require a source of stored energy.

EP-A-567,348 describes a metering valve for an aerosol container having a two stage compress and release mechanism to fill the valve and dispense therefrom. The valve includes metering and dispensing members connected by a central bellows assembly or flexible membrane for relative linear movement into and out of positive sealing engagement with oppositely facing valve seats provided on a fixed valve housing and the metering member respectively. The metering valve herein requires no such central bellows feature.

According to the present invention there is provided a metering valve for an aerosol container comprising a valve body defining a metering chamber, said metering chamber having an inlet and an outlet, said inlet permitting flow of aerosol from said container to the metering chamber and said outlet permitting dispensing of aerosol from the metering chamber, the inlet having an inlet valve reversibly actuable from an open to a closed position; and the outlet having an outlet valve reversibly actuable from a dispensing to a non-dispensing position, wherein said outlet valve comprises a outlet valve seat and an outlet valve poppet in biasable contact therewith.

As used herein the term valve poppet means any element which is receivable by a valve seat to form a valve seal and which is movable from the valve seat to break the valve seal. The valve poppet can be of essentially any suitable shape. The biasable contact between the outlet valve seat and outlet valve poppet may be provided by any suitable biasing means, such as a spring.

The metering valve herein enables dispensing of aerosol contents without the need for movement of a dispensing member relative to the valve body. In particular, the metering valve herein does not require the sliding or rotary movement of a valve stem relative to the valve body.

The metering valve herein is preferably designed to provide a non-convoluted flow passageway from the inlet to the outlet of the metering chamber.

Preferably, the metering valve forms a single integral unit which may conveniently be fitted onto known aerosol containers for use in the dispensing of medicament.

Preferably, the inlet valve comprises an inlet valve seat and an inlet valve poppet in biasable contact therewith. The biasable contact may be provided by any suitable biasing means (e.g. a spring).

Preferably, either one of the inlet and outlet valves is closed when the metering valve is in a rest position. More preferably both the inlet and outlet valves are closed when the metering valve is at rest.

Preferably, the inlet and outlet valves are operable independently. Their operation may however, be coupled by using of a suitably coupled trigger system.

In one aspect, any valve poppet comprises a hard, incompressible material and any valve seat comprises a softer, compressible material. In another aspect, any valve poppet comprises a soft, compressible material and any valve seat comprises a harder, incompressible material.

Alternatively, the inlet and outlet valve poppets and respective valve seats may both comprise hard, incompressible materials having smooth surfaces to ensure good sealing.

Preferably, the valve additionally comprises an outlet valve mover for moving the outlet valve poppet out of contact with the outlet valve seat.

Preferably, the valve additionally comprises an inlet valve mover for moving the inlet valve poppet out of contact with the inlet valve seat.

In one aspect, either or both of said inlet valve mover or said outlet valve mover is mechanically actuable. That is to say, actuable by application of mechanical force either directly or through a mechanism capable of transferring mechanical force.

In another aspect, either or both of the inlet valve mover or the outlet valve mover is electrically actuable. That is to say actuable by application of electrical current. More preferably, either or both of the inlet valve mover or the outlet valve mover comprises a multi-component strip or wire which is deformable in response to electrical current flow.

Suitable multi-component strips typically comprise a plurality of layers of material, each material having a different coefficient of thermal expansion. Preferred examples of multi-component strips include strips comprising multiple layers of different metals (e.g. bimetallic strips) and strips comprising at least one piezoelectric or piezoresistive material. Suitable piezoelectric materials include piezoelectric ceramics, such as compounds of lead zirconate and lead titonate, and piezoelectric crystals which are generally polycrystalline ferroelectric materials with the perovskite structure.

Suitable multi-component wires comprise an alloy which undergoes a phase transition on heating which results in contraction thereof. Typically the degree of contraction is from 2% to 8%. Such alloys are generally known as shape memory alloys. Certain shape memory alloys also undergo a change in shape on recooling. Such two way shape memory alloys are also envisaged for use herein.

In one embodiment, the alloy is preferably a nickel-titanium alloy such as a nickel-titanium alloy comprising from 5% to 95%, preferably from 20% to 80%, nickel by weight and from 95% to 5%, preferably from 80% to 20%, titanium by weight. By nickel-titanium alloy it is meant an alloy comprised essentially of nickel and titanium, although other elements may be present in small (e.g. trace) amounts.

In other embodiments, the alloy is preferably a copper-aluminium-nickel alloy or a copper-zinc-aluminium alloy. Trace amounts of other elements may also be present.

Suitable wires typically have a diameter from 30 to 400 micrometers, preferably from 50 to 150 micrometers.

Preferably, either or both of the inlet valve mover or the outlet valve mover is magnetically actuable.

Preferably, either or both of the inlet valve mover or the outlet valve mover compresses magnetic material or material which is magnetically inductive, that is to say material into which magnetism can be induced. The material may be permanently or non-permanently magnetisable.

Preferably, either or both of the inlet valve mover or the outlet valve mover is pneumatically actuable.

Preferably, either or both of the inlet valve mover or the outlet valve mover is hydraulically actuable. More preferably, either or both of the inlet valve mover or the outlet valve mover comprises means, such as a fluid-filled bag or tube capable of transferring hydraulic force.

Preferably, the outlet valve poppet and/or the inlet valve poppet comprises an element in the form of a ball, a mushroom, a cone, a disc or a plug.

Preferably, the valve body additionally defines a sampling chamber and the inlet permits flow from the sampling chamber to the metering chamber.

The metering chamber is preferably shaped to minimise the surface contact area with the aerosol and thereby reduce deposition of medicament thereon.

In one aspect, the metering chamber has a fixed volume.

In another aspect, the metering chamber is of variable volume. The volume of the metering chamber may for example be varied to provide the optimum amount of medicament for release. In one preferred aspect, the volume of the metering chamber is variable automatically in response to a dosing signal sent from an electronic information process or.

Various types of variable volume metering chambers are envisaged. Suitable chambers comprise a fixed volume chamber whose metering volume is variable by insertion of a plunger or piston. The piston or plunger may have fixed form or alternatively may comprises an element of variable shape and volume such as an inflatable balloon. Other suitable chambers comprise a chamber which is expandable because it is formed from a flexible/expandable material. Further suitable chambers have telescopic or concertina arrangements to allow for mechanical expansion of the metering volume.

According to another aspect of the present invention there is provided an aerosol container comprising a metering valve as described above.

In a preferred aspect the valve body of the metering valve is not movable relative to the container. Also, the metering valve contains no movable stem. This contrasts with current slide valves where actuation of the valve is achievable by relative movement of the aerosol container to the valve stem.

In one aspect, the aerosol container comprises a suspension of a medicament in a propellant. More preferably, the propellant is liquefied HFA134a, HFA-227 or carbon dioxide. More preferably, the medicament is selected from the group consisting of albuterol, salmeterol, fluticasone propionate, beclomethasone dipropionate, salts or solvates thereof and any mixtures thereof.

In another aspect, the aerosol container comprises a compressed gas, preferably compressed air.

According to a further aspect of the present invention there is provided an inhalation device for dispensing medicament to a patient comprising a housing; an aerosol container, locatable within said housing, said aerosol container comprising a metering valve as described above; and an outlet valve trigger for triggering the movement of the outlet valve poppet out of contact with the outlet valve seat.

When the aerosol container comprises an inlet poppet valve the inhalation device preferably also comprises an inlet valve trigger for triggering the movement of the inlet valve poppet out of contact with the inlet valve seat.

Preferably, either or both of said outlet valve trigger or said inlet valve trigger is triggerable in response to the breath of a patient. The outlet valve or inlet valve triggers may be triggerable in response to the inward breath of the patient, or alternatively triggerable at a trigger point which is coupled to the end of the exhalation part of the patient's breath cycle. Inhalation devices which are triggerable at the end of the exhalation part of the breath cycle are described in UK patent application no. 9905134.4.

Preferably, either or both of the outlet valve trigger or the inlet valve trigger communicates with a sensor which senses the breath of a patient.

In one aspect, the sensor comprises a breath-movable element which is movable in response to the breath of a patient. Preferably, the breath-movable element is selected from the group consisting of a vane, a sail, a piston and an impeller.

In another aspect, the sensor comprises a pressure sensor for sensing the pressure profile associated with the breath of a patient.

In a further aspect, the sensor comprises an airflow sensor for sensing the airflow profile associated with the breath of a patient.

In a further aspect, the sensor comprises a temperature sensor for sensing the temperature profile associated with the breath of a patient.

In a further aspect, the sensor comprises a moisture sensor for sensing the moisture profile associated with the breath of a patient.

In a further aspect, the sensor comprises a gas sensor for sensing the oxygen or carbon dioxide profile associated with the breath of a patient.

In a further aspect, the sensor comprises a piezoelectric or piezoresistive element.

The outlet valve trigger and the inlet valve trigger may be independently triggerable or they may be triggerable in a coupled fashion.

Preferably, either or both of the outlet valve trigger or the inlet valve trigger is a mechanical trigger. In one aspect, the mechanical trigger comprises a lever mechanism. In another aspect, the mechanical trigger comprises a torque 110 transfer mechanism.

Preferably, either or both of the outlet valve trigger or the inlet valve trigger comprises comprises a multi-component strip which is deformable in response to electrical current flow. The multi-component strip typically comprises a plurality of layers of material, each material having a different coefficient of thermal expansion. Preferred examples of multi-component strips include strips comprising multiple layers of different metals (e.g. bimetallic strips) and strips comprising at least one piezoelectric or piezoresistive material.

Preferably, either or both of the outlet valve trigger or the inlet valve trigger is a magnetic trigger.

In one aspect, the outlet valve trigger interacts magnetically with the outlet valve poppet and/or the inlet valve trigger interacts magnetically with the inlet valve poppet.

In another aspect, the outlet valve trigger interacts magnetically with a outlet shuttle contacting the outlet valve poppet and/or the inlet valve trigger interacts magnetically with an inlet shuttle contacting the inlet valve poppet. Preferably, the outlet shuttle and/or inlet shuttle comprises magnetic material.

In a further aspect, the outlet shuttle comprises material which is magnetically inductive and the outlet valve trigger comprises an inductive element capable of inducing magnetism therein and/or the inlet shuttle comprises material which is magnetically inductive and the inlet valve trigger comprises an inductive element capable of inducing magnetism therein.

Preferably, either or both of the outlet valve trigger or the inlet valve trigger is a pneumatic trigger.

Preferably, either or both of the outlet valve trigger or the inlet valve trigger is a hydraulic trigger. More preferably, the hydraulic trigger comprises a fluid-filled bag or tube capable of transferring hydraulic force.

The invention will now be described further with reference to the accompanying drawing in which.

Figure 5A:
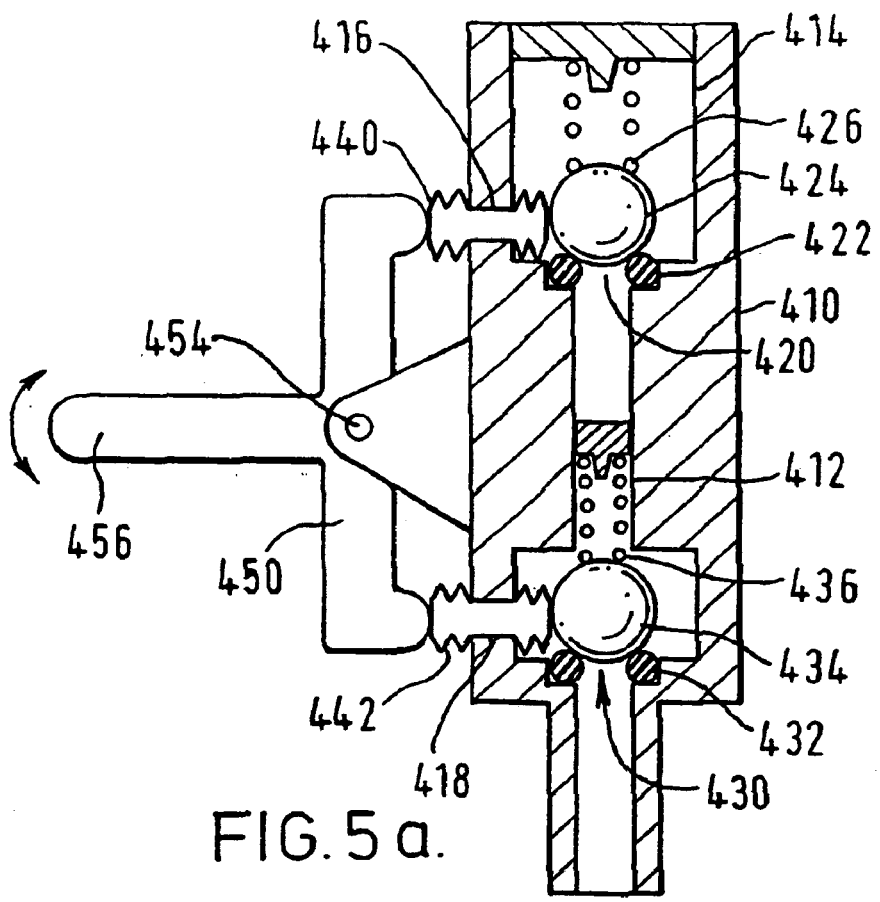
Figure 5B:
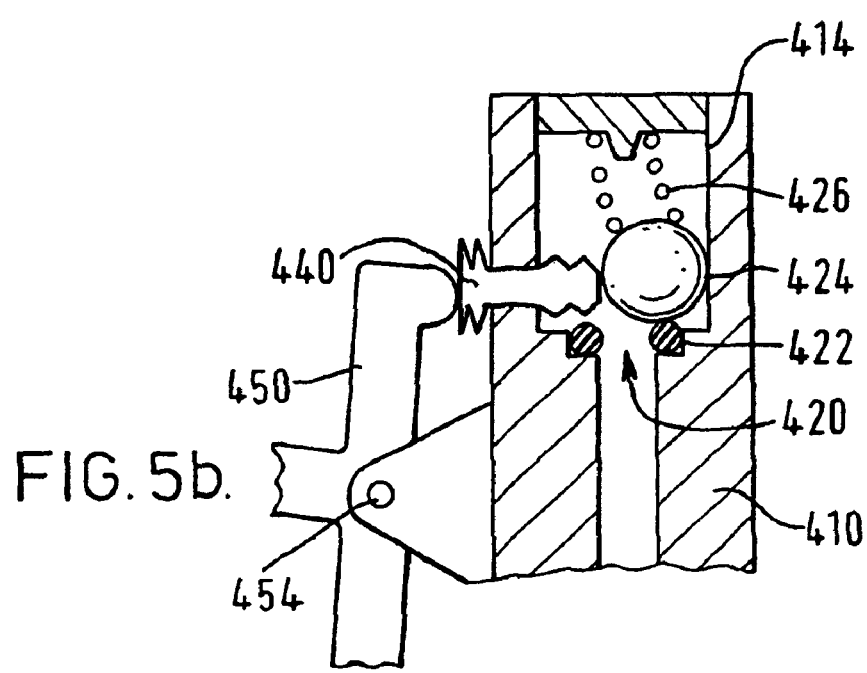
Figure 6:
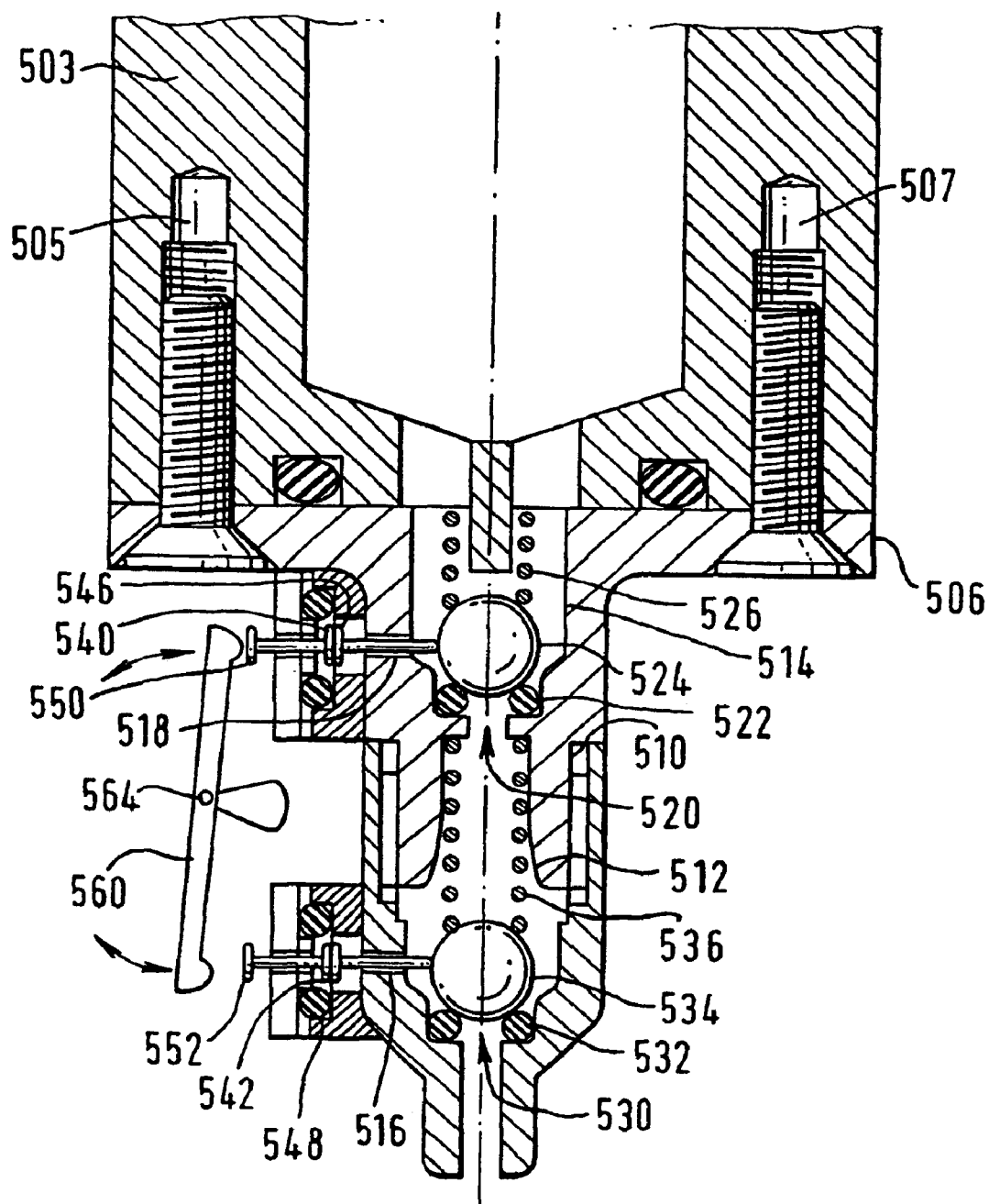
Figure 7:
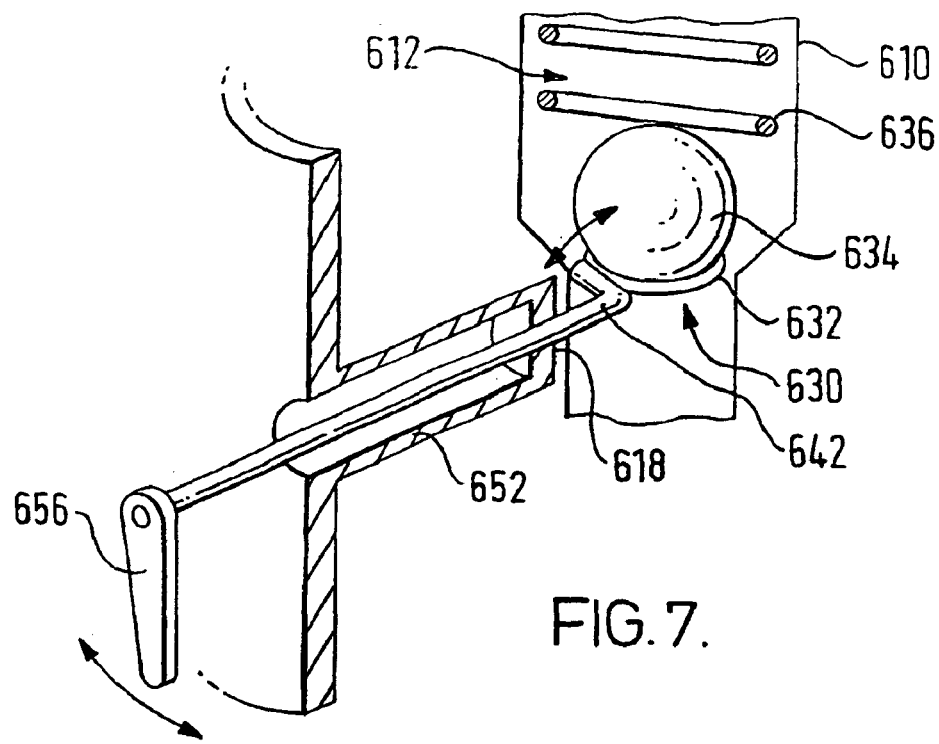
Figure 9:
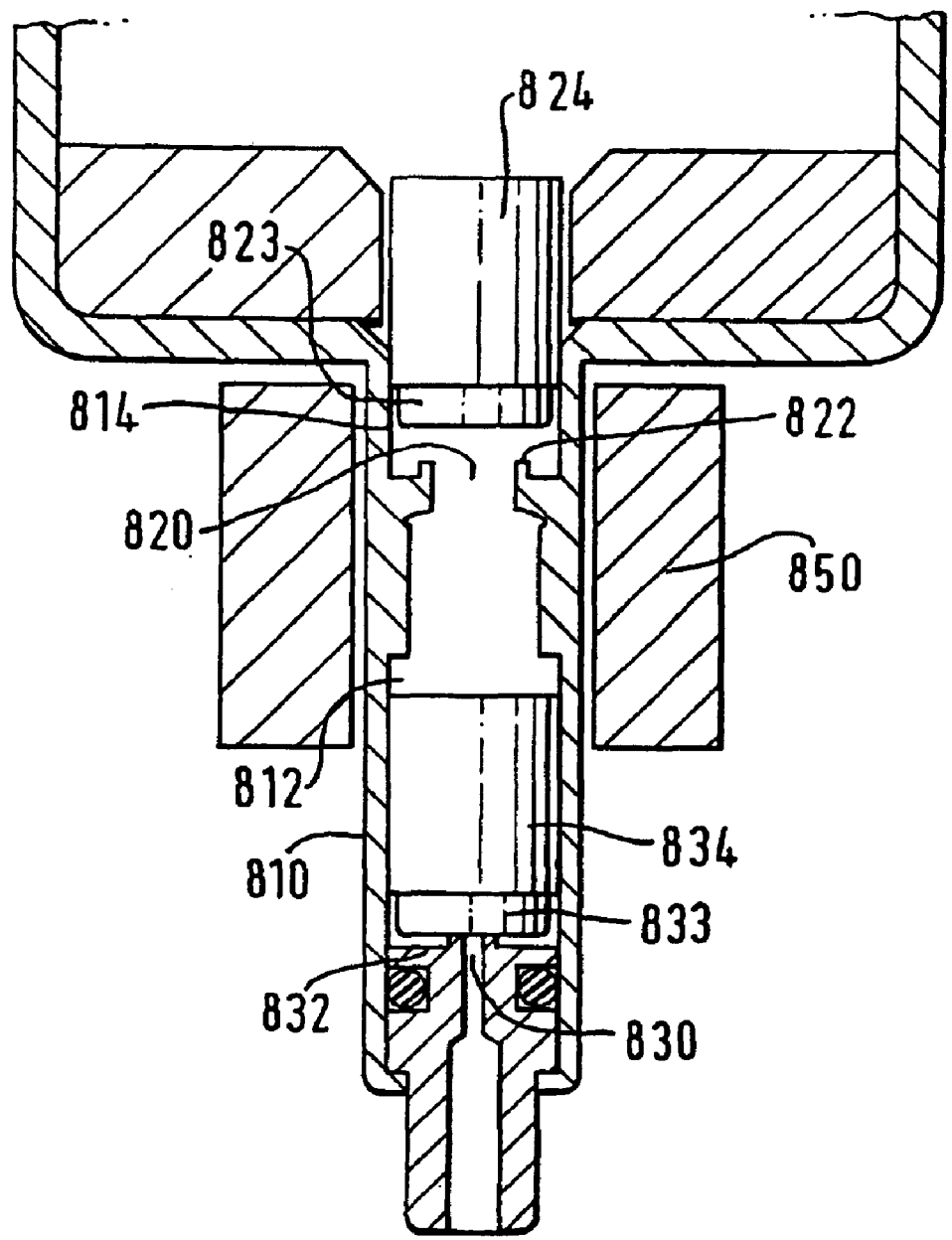

FIG. 5*a* is a sectional view of a fifth metering valve in accord with the present invention;

FIG. 5*b* is a sectional view of a detail of the valve of FIG. 5*a*;

FIG. 6 is a sectional view of a sixth metering valve in accord with the present invention;

FIG. 7 is a plan view of the valve actuation mechanism of a seventh metering valve in accord with the present invention;

FIGS. 8*a* to 8*d* show various forms of poppet valve suitable for use in accord with the invention;

FIG. 9 is a sectional view of an eighth metering valve in accord with the invention.

Figure 10:
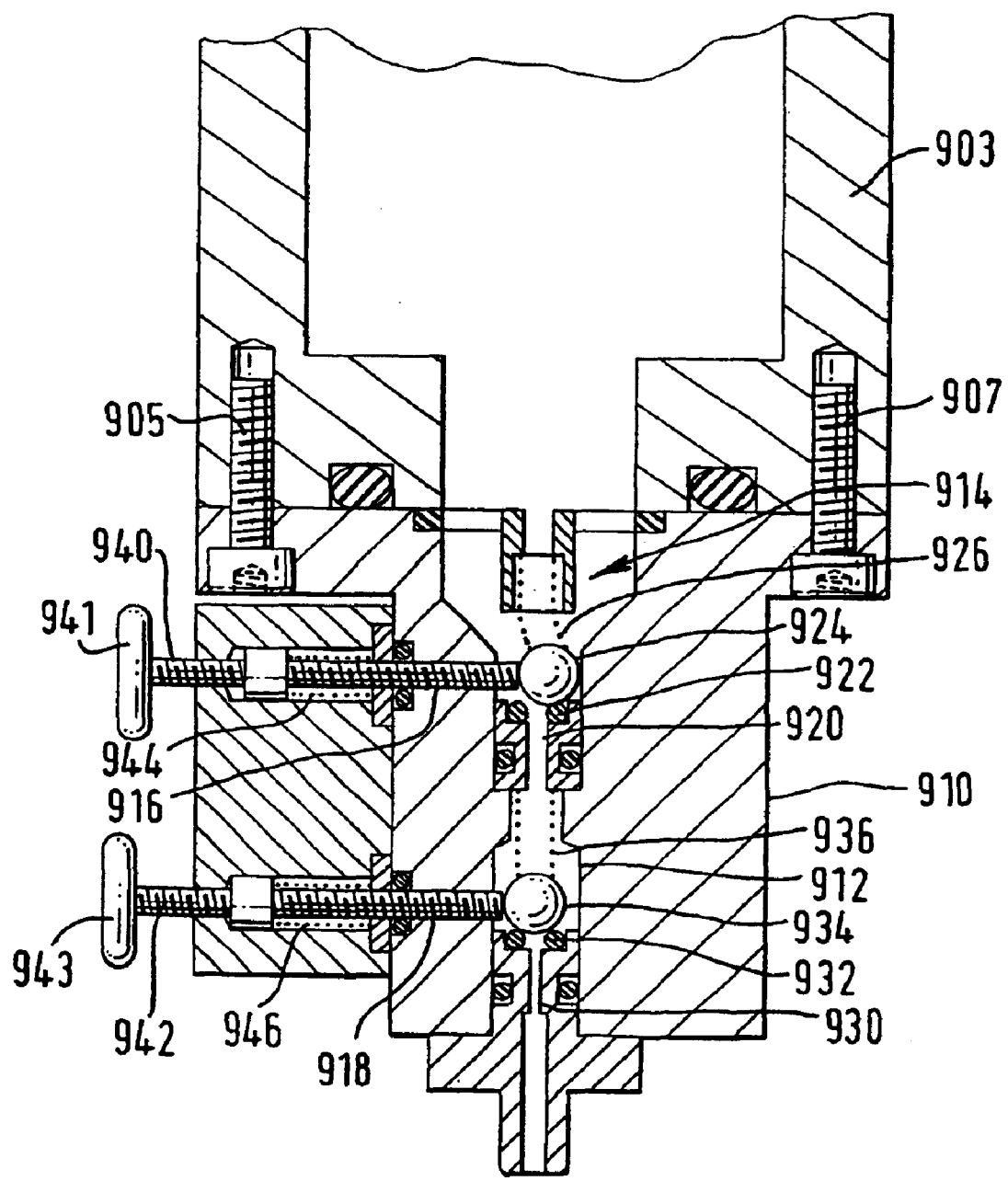
Figure 11:
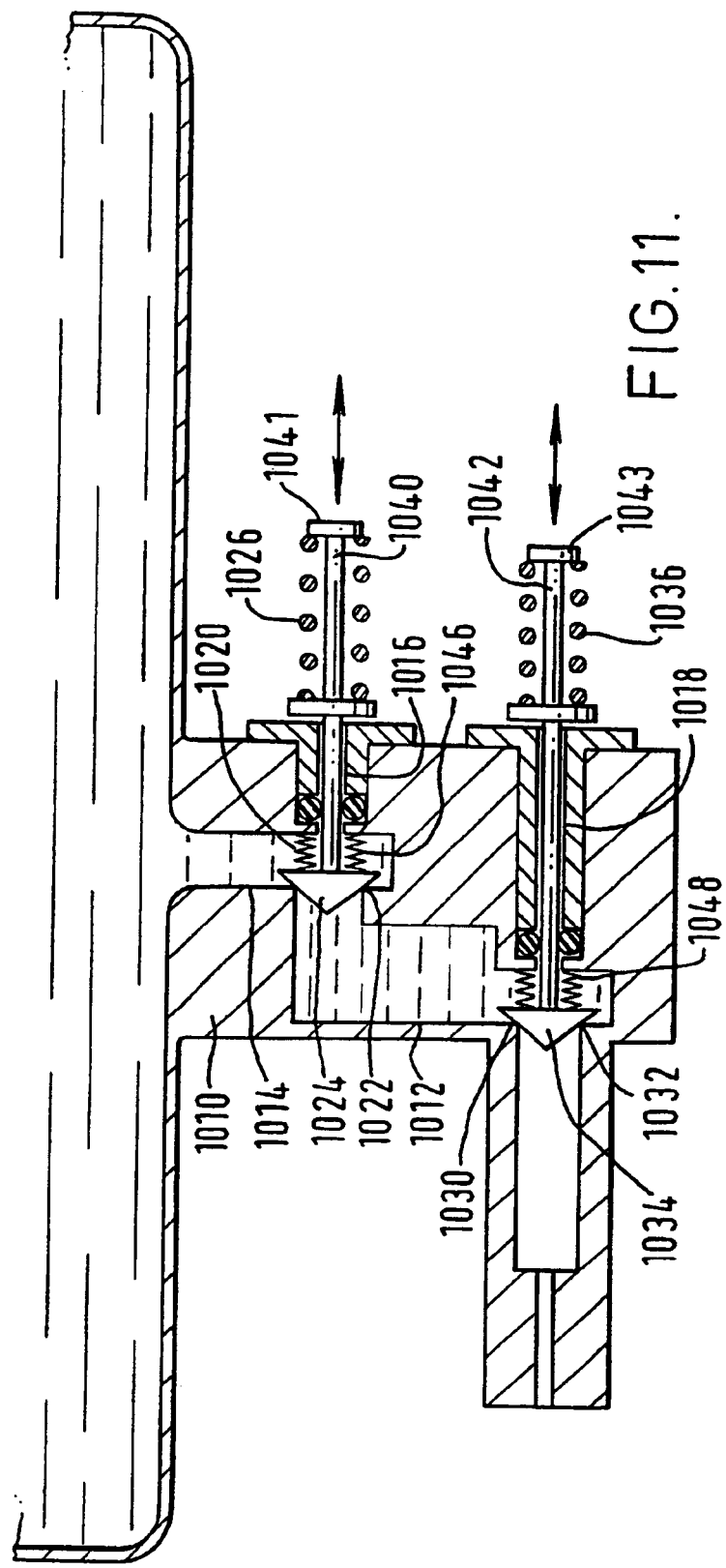
Figure 12:
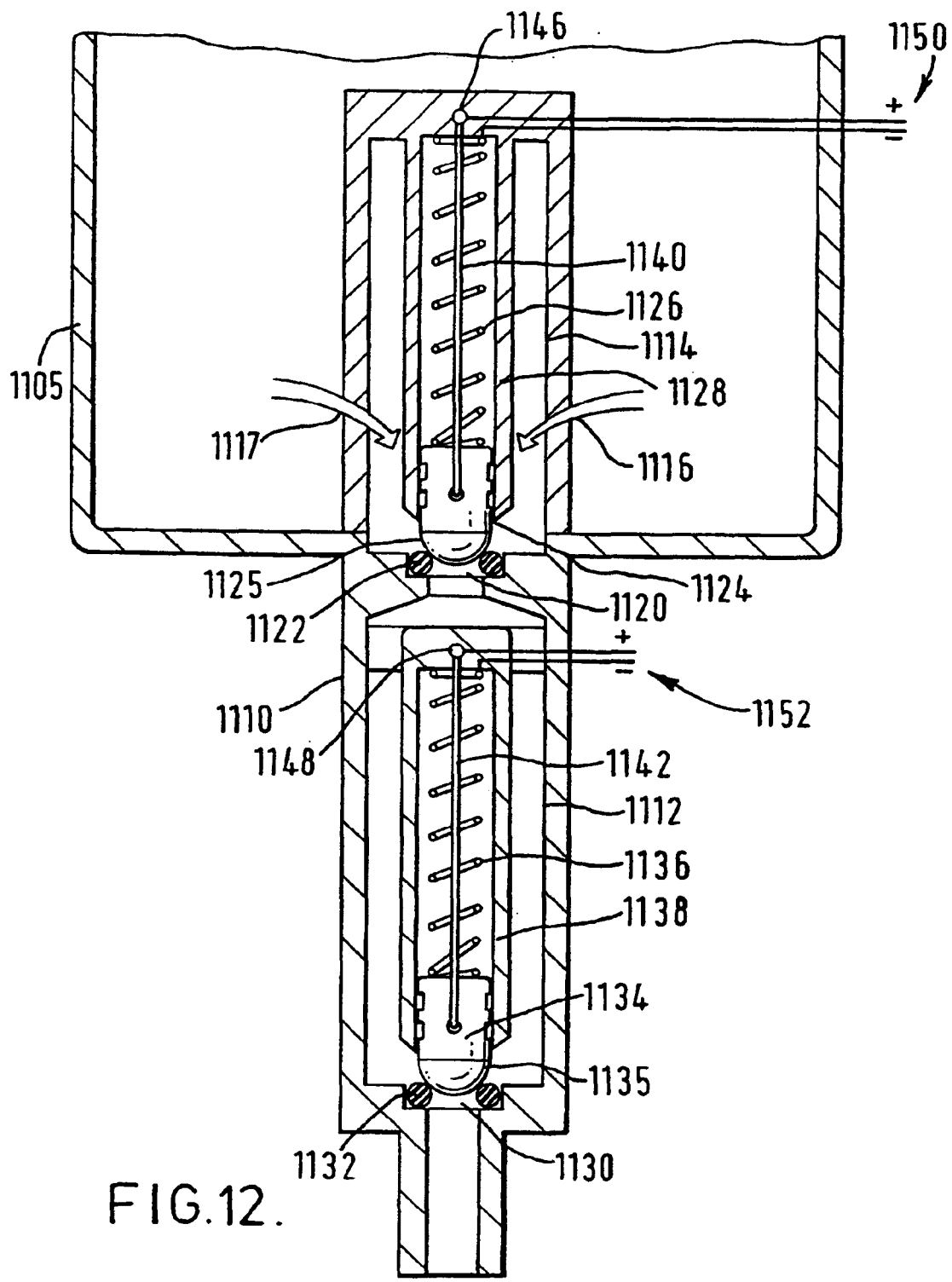
Figure 13:
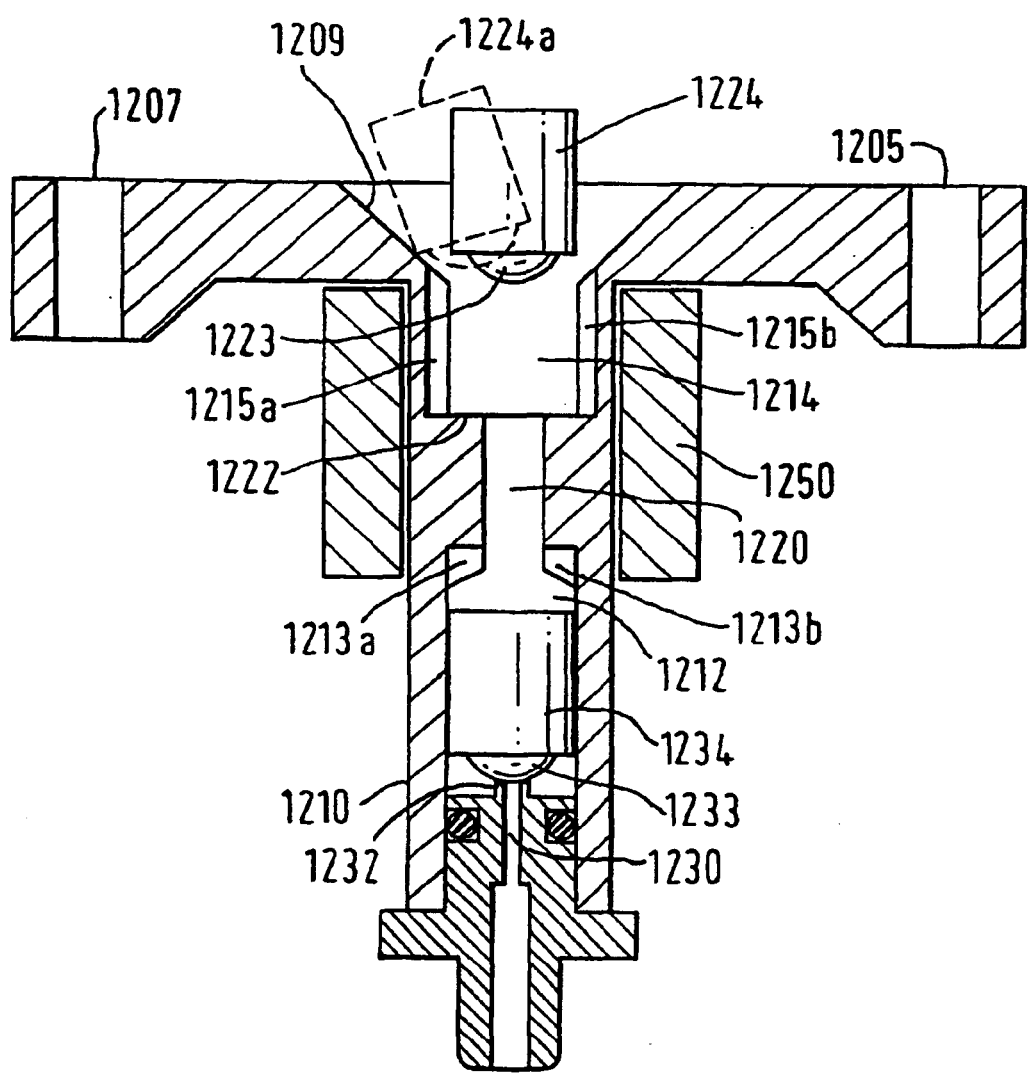
Figure 14:
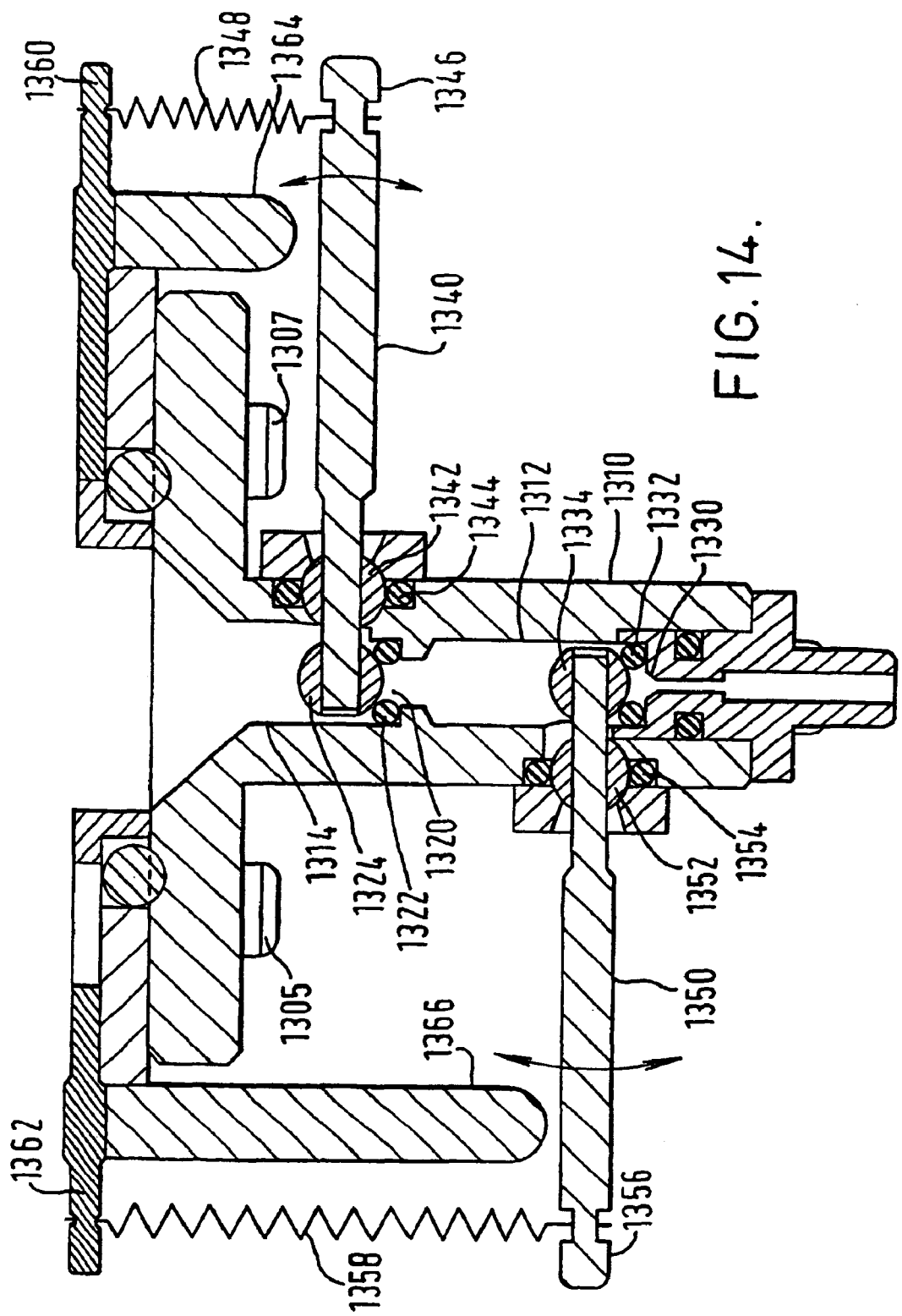
Figure 15:
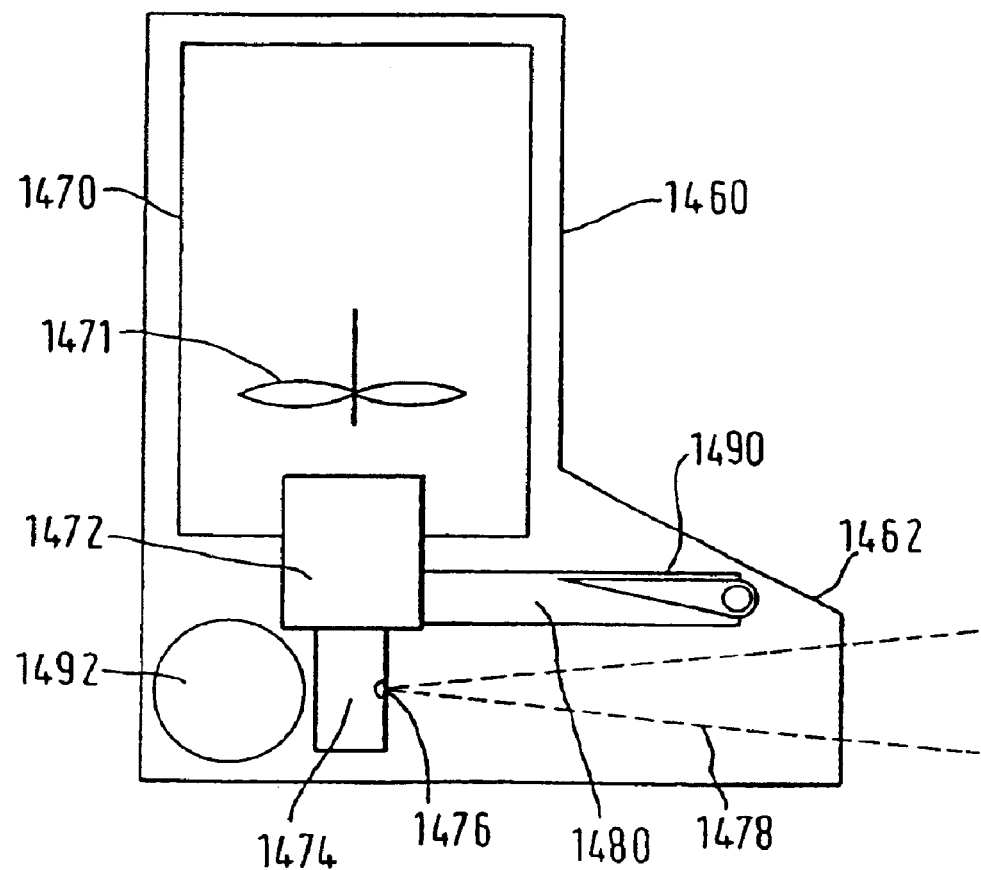

FIG. 10 is a sectional view of a ninth metering valve in accord with the invention;

FIG. 11 is a sectional view of a tenth metering valve in accord with the invention;

FIG. 12 is a sectional view of an eleventh metering valve in accord with the invention;

FIG. 13 is a sectional view of a twelfth metering valve in accord with the invention;

FIG. 14 is a sectional view of a thirteenth metering valve in accord with the invention; and FIG. 15 is a schematic view of an inhalation device in accord with the present invention.

Figure 1:
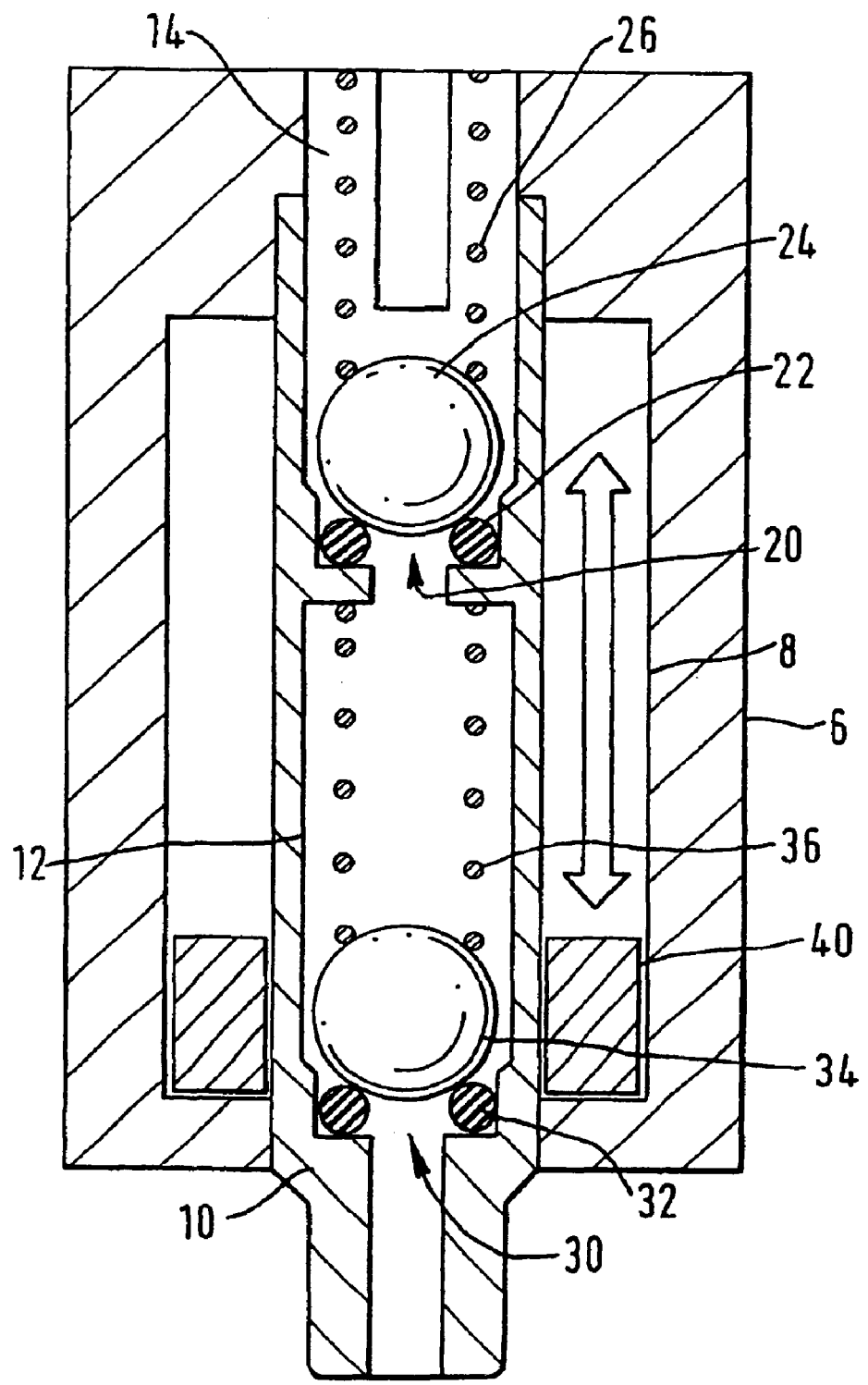
FIG. 1 is a sectional view of a first metering valve in accord with the present invention.

FIG. 1 shows an aerosol metering valve herein. The valve comprises a valve body 10 which defines a metering chamber 12 and a sampling chamber 14. The metering chamber 12 has an inlet 20 permitting flow of aerosol from the sampling chamber 14 which in turn receives aerosol from a container (not shown) and an outlet 30 permitting dispensing of aerosol from the metering chamber 12. The inlet 20 is provided with valve means comprising a valve seat 22 and a valve poppet in the form of a metal ball 24. The metal ball 24 is biased towards the valve seat 22 by the action of spring 26. The outlet 30 is also provided with valve means comprising a valve poppet in the form of a metal ball 34 held by a spring 36 in biased contact with a valve seat 32. The valve body 10 is within a housing 6 shaped such as to define a circular track 8 running upwardly in parallel with the exterior of the valve body 10. Within the track 8 is contained a magnetic ring 40 which is movable up and down the track 8.

Actuation of the valve of FIG. 1 is achievable by movement of the magnetic ring 40 which can magnetically interact with the metal ball poppets 24,34 to dislodge them from their seats 22, 32. Movement of magnetic ring itself is for example, achievable by use of a second magnet (not shown). In a typical operation the inlet 20 valve will first be opened to allow metered flow of aerosol from the sampling chamber 14 into the metering chamber 12. The outlet 30 valve is then opened to allow for dispensing of the aerosol.

Figure 2:
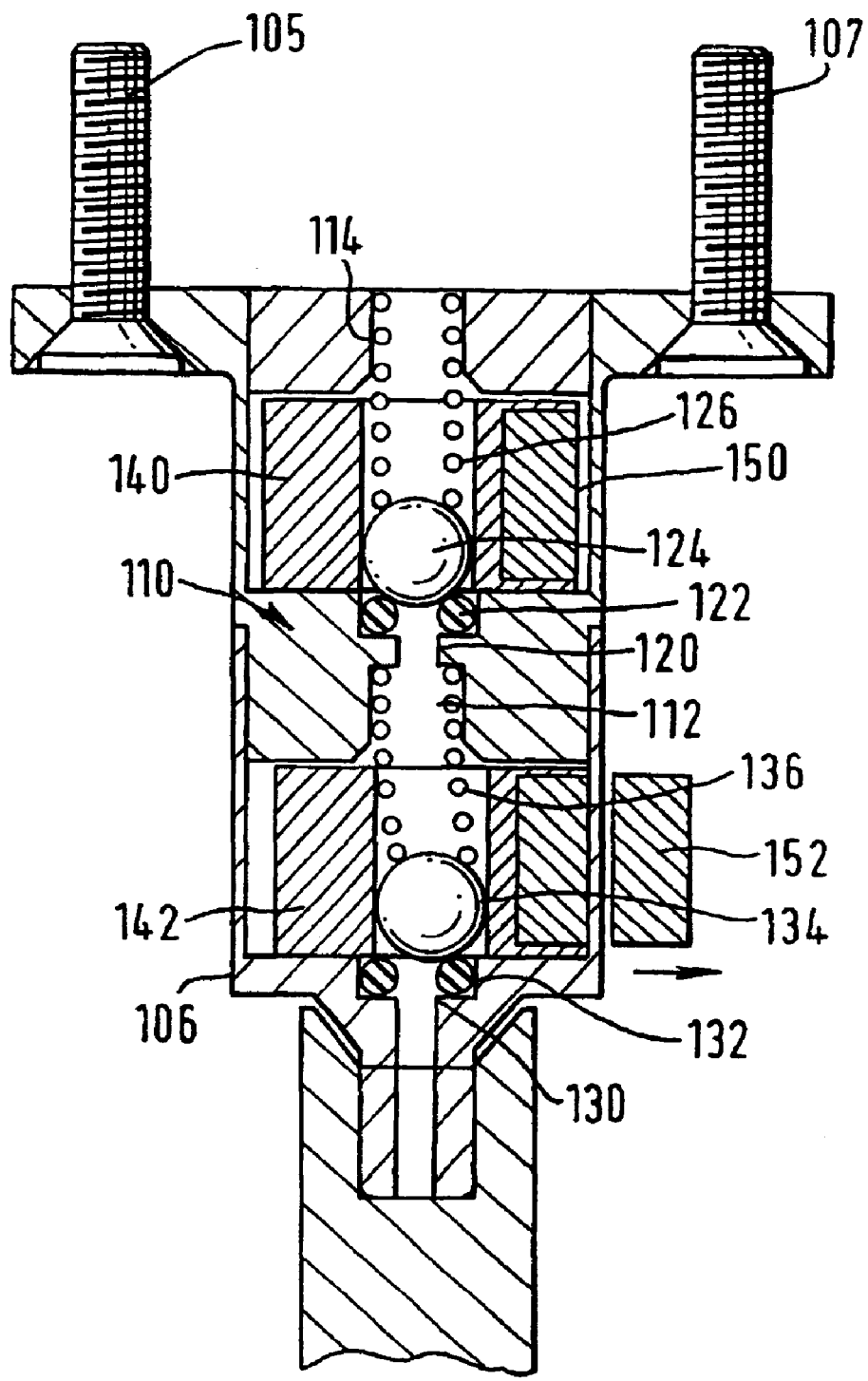
FIG. 2 is a sectional view of a second metering valve in accord with the present invention.

FIG. 2 shows an aerosol metering valve herein. The valve comprises a valve body 110 which defines a metering chamber 112 and a sampling chamber 114. The metering chamber has an inlet 120 permitting flow of aerosol from the sampling chamber 114 and an outlet 130 permitting dispensing of aerosol from the metering chamber 112. The inlet 120 is provided with valve means comprising a valve seat 122 and a valve poppet in the form of a resilient ball 124. The ball 124 is biased towards the valve seat 122 by the action of spring 126. The outlet 130 is also provided with valve means comprising a valve poppet in the form of a ball 134 biased into contact with a valve seat 132 by action of spring 136. The valve body 110 is within housing 106 and the housing is provided with fixing screws 105, 107 for fixing the valve to an aerosol container (not shown). Movable magnetic rings 140, 142 contact the resilient balls 124, 134 of the inlet 120 and outlet 130 valves respectively. The magnetic rings 140, 142 are in turn in magnetic communication with shuttle magnets 150 and 152.

Actuation of the metering valve of FIG. 2 is achievable by movement of the magnetic rings 140, 142 to physically dislodge the resilient balls 124, 134 from their respective seats 122, 132. Movement of magnetic rings is achievable by movement of the shuttle magnets 150, 152. The shuttle magnets 150, 152 may, in turn be coupled to a mechanical trigger such as a lever mechanism (not shown). In a typical operation the inlet 120 valve will first be opened to allow metered flow of aerosol from the sampling chamber 114 into the metering chamber 112. The outlet 130 valve is then opened to allow for dispensing of the aerosol.

Figure 3:
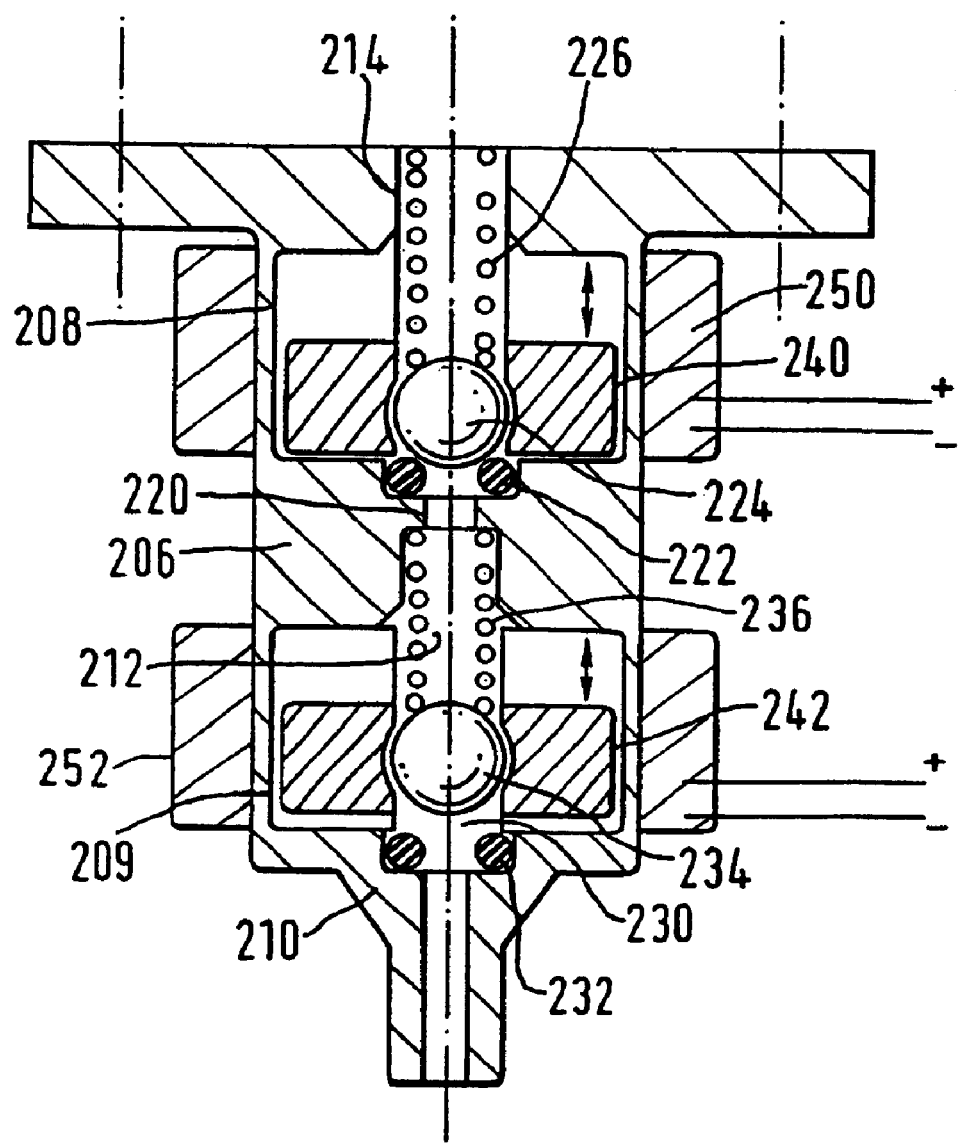
FIG. 3 is a sectional view of a third metering valve in accord with the present invention.

FIG. 3 shows an aerosol metering valve herein. The valve comprises a valve body 210 which defines a metering chamber 212. The metering chamber has an inlet 220 permitting flow of aerosol from a container (not shown) and an outlet 230 permitting dispensing of aerosol from the metering chamber 212. The inlet 220 is provided with valve means comprising a valve seat 222 and a valve poppet in the form of a resilient plastic ball 224. The ball 224 is biased towards the valve seat 222 by the action of spring 226. The outlet 230 is also provided with valve means comprising a valve poppet in the form of a resilient plastic ball 234 biased into contact with a valve seat 232 by action of spring 236. The valve body 210 is within a housing 206. The housing 206 shaped is such as to define two circular cavities 208, 209, each running upwardly in parallel with a portion of the exterior of the valve body 210 and respectively positioned around the inlet 220 and outlet 230 valves. First and second circular solenoid cores 240, 242 are movably located within the first and second circular cavities 208, 209 and respectively engage the inlet and outlet ball valves 224, 234. The circular solenoid cores 240, 242 are in turn, positioned for inductive communication with outer solenoid coil windings magnets 250 and 252. The solenoid coil windings 250, 252 are connected to an electrical power source (not shown).

Actuation of the metering valve of FIG. 3 is achievable by movement of the circular solenoid cores 240, 242 to physically dislodge the resilient balls 224, 234 in an upward direction from their respective seats 222, 232. Movement of the circular solenoid cores 240, 242 is in turn achievable by the application of electrical current to the solenoid coil windings 250, 252. In a typical operation the inlet 220 valve will first be opened to allow metered flow of aerosol into the metering chamber 212. The outlet 230 valve is then opened to allow for dispensing of the aerosol.

Figure 4:
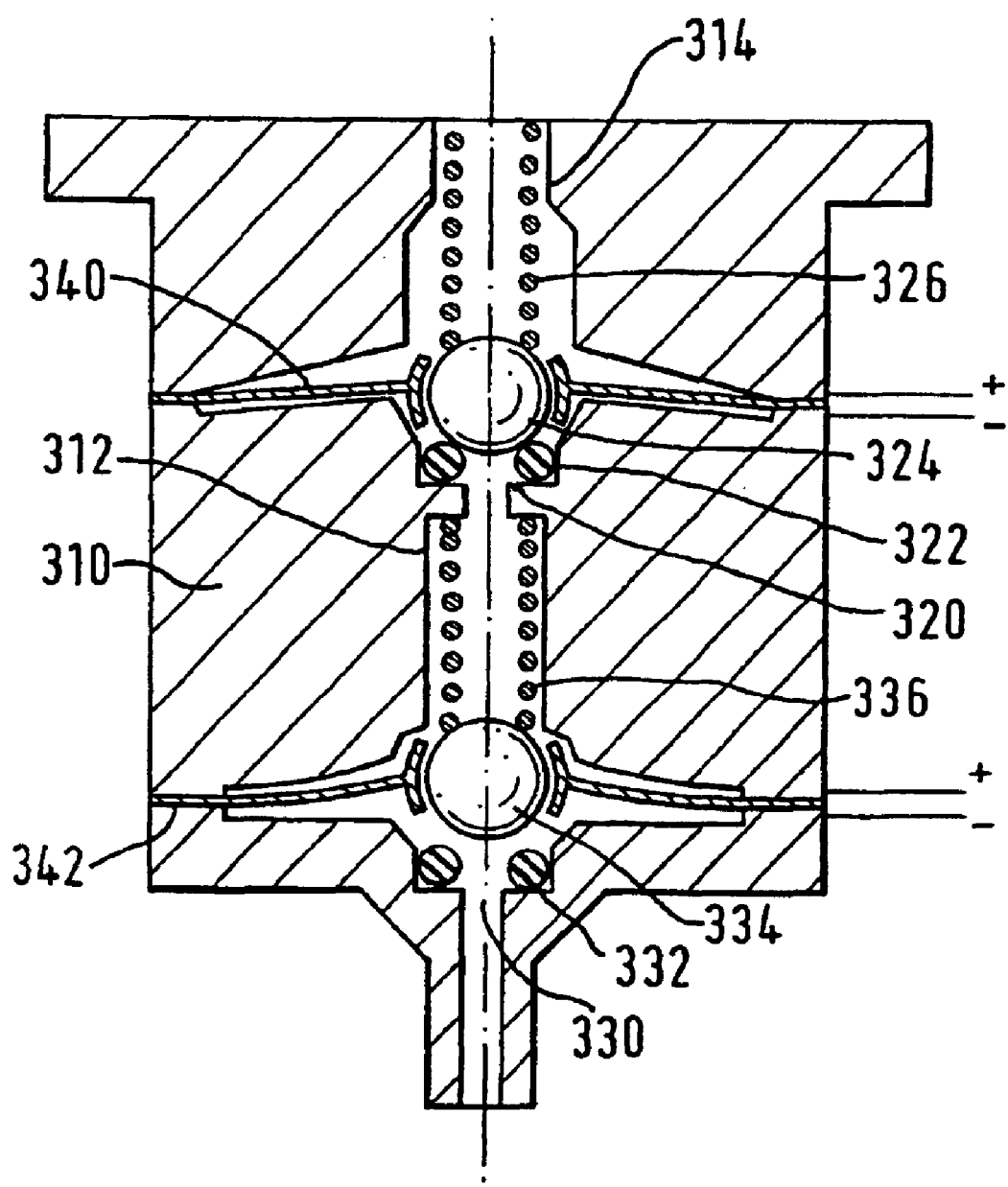
FIG. 4 is a sectional view of a fourth metering valve in accord with the present invention.

FIG. 4 shows an aerosol metering valve herein. The valve comprises a valve body 310 which defines a metering chamber 312 and a sampling chamber 314. The metering chamber 312 has an inlet 320 permitting flow of aerosol from the sampling chamber 314 and an outlet 330 permitting dispensing of aerosol from the metering chamber 312. The inlet 320 is provided with valve means comprising a valve seat 322 and a valve poppet in the form of a resilient ball 324. The ball 324 is biased towards the valve seat 322 by the action of spring 326. The outlet 330 is also provided with valve means comprising a valve poppet in the form of a resilient ball 334 biased into contact with a valve seat 332 by action of spring 336. Gripping arms 340, 342 grip the resilient balls 324, 334 of the inlet 320 and outlet 330 valves respectively. The gripping arms are formed from a bimetallic strip wherein each of the bimetallic components thereof has a different coefficient of thermal expansion. The gripping arms 340, 342 are connectable to an electrical power source (not shown).

Actuation of the metering valve of FIG. 4 is achievable by movement of the gripping arms 340, 342 to physically dislodge the resilient balls 324, 334 from their respective seats 322, 332. Movement of the gripping arms 340, 342 is in turn achievable by the application of electrical current which causes deformation of the bimetallic strip from which the arms 340, 342 are formed. In a typical operation the inlet 320 valve will first be opened to allow metered flow of aerosol into the metering chamber 312. The outlet 330 valve is then opened to allow for dispensing of the aerosol.

FIG. 5a shows an aerosol metering valve herein and FIG. 5b shows a detail of this valve when the inlet valve is in the open position. The metering valve comprises a valve body 410 which defines a metering chamber 412 and a sampling chamber 414. The metering chamber has an inlet 420 permitting flow of aerosol from the sampling chamber 414 and an outlet 430 permitting dispensing of aerosol from the metering chamber 412. The inlet 420 is provided with valve means comprising a valve seat 422 and a valve poppet in the form of a resilient ball 424. The ball 424 is biased towards the valve seat 422 by the action of spring 426. The outlet 430 is also provided with valve means comprising a valve poppet in the form of a resilient ball 434 biased into contact with a valve seat 432 by action of spring 436. Shaped, flexible elastomer bags 440, 442 sit within and on both sides of access holes 416,418 provided in the sampling chamber 414 and metering chamber 412 respectively. The elastomer bags 440, 442 contain fluid material. It may be seen that one portion of each of the elastomer bags 440, 442 contacts the resilient balls 424, 434 of the inlet 420 and outlet 430 valves respectively. It may also be seen that another portion of each of the elastomer bags 440, 442 contacts an impacting arm 450 which is pivoted at pivot 454. The impacting arm 450 is itself connected to handle 456 which may itself be attached to a breath-actuable vane (not shown).

Actuation of the metering valve of FIGS. 5a and 5b is achievable by impacting the flexible, fluid-filled elastomer bags 440, 442 to physically dislodge the resilient balls 424,434 from their respective seats 422, 432. Impaction of the elastomer bags 440, 442 is in turn achievable by the impacting movement of the impacting arm 450. The bags 440, 442 are shaped such as to deform upon impact to allow for transfer of the energy of impaction through the fluid contents.

The deformation of one of the bags 440 on being struck by the impacting arm 450 is shown in FIG. 5b which also shows the dislodgement of the resilient ball 424 from its seat 422. In a typical operation the inlet 420 valve will first be opened to allow metered flow of aerosol into the metering chamber 412. The outlet 430 valve is then opened to allow for dispensing of the aerosol. It will be appreciated that the illustrated pivotal mounting 454 of the impacting arm 450 only allows for impaction of one of the elastomer bags 440,442, and hence opening of only one of the inlet 420 or outlet 430 valves, at a time.

FIG. 6 shows an aerosol metering valve herein. The valve comprises a valve body 510 which defines a metering chamber 512 and a sampling chamber 514. The metering chamber has an inlet 520 permitting flow of aerosol from the sampling chamber 514 and an outlet 530 permitting dispensing of aerosol from the metering chamber 512. The inlet 520 is provided with valve means comprising a valve seat 522 and a valve poppet in the form of a resilient ball 524. The ball 524 is biased towards the valve seat 522 by the action of spring 526. The outlet 530 is also provided with valve means comprising a valve poppet in the form of a ball 534 biased into contact with a valve seat 532 by action of spring 536. The valve body 510 is within a housing 506 and the housing is provided with fixing screws 505, 507 for fixing the valve to an aerosol container 503 (shown in part only). Shaped pins 540, 542 sit within and on both sides of access holes 516, 518 provided in the sampling chamber 514 and metering chamber 512 respectively. It may be seen that the tail end of each of the shaped pins 540, 542 contacts the resilient balls 524, 534 of the inlet 520 and outlet 530 valves respectively. It may also be seen that the head of each of the pins 540, 542 contacts an elastomer diaphragm 546,548 which in turn contacts double-headed transfer pins 550, 552. The elastomer diaphragms 546,548 and the transfer pins 550, 552 are mounted in side compartments of the valve body. The outer heads of the transfer pins 550, 552 are impactable by an impacting arm 560 which is pivoted at pivot 564. The impacting arm 560 may itself be connected to a breath-actuable vane (not shown).

Actuation of the metering valve of FIG. 6 is achievable by movement of the shaped pins 540, 542 to physically dislodge the resilient balls 524, 534 from their respective seats 522, 532. Movement of the shaped pins 540, 542 is in turn achievable by impacting the elastomer diaphragms 546, 548 with their respective transfer pins 550, 552 following an impact by the impacting arm 560. In a typical operation the inlet 520 valve will first be opened to allow metered flow of aerosol into the metering chamber 512. The outlet 530 valve is then opened to allow for dispensing of the aerosol. It will be appreciated that the illustrated pivotal mounting 564 of the impacting arm 560 only allows for impaction of one of the transfer pins 550,552, and hence opening of only one of the inlet 520 or outlet 530 valves, at a time.

FIG. 7 shows a simplified, schematic representation of a poppet valve actuation mechanism suitable for use in an aerosol metering valve herein. The metering valve might, for example be of a type similar to those shown in FIGS. 1 to 6 but including the poppet valve actuation mechanism now described. The portion of the valve body 610 which defines a metering chamber 612 is shown. The metering chamber has an outlet 630 permitting dispensing of aerosol from the metering chamber 612. The outlet 630 is provided with valve means comprising a valve poppet in the form of a resilient ball 634 biased into contact with a valve seat 632 by action of spring 636. An actuator rod 642 sits within and on both sides of an access hole 618 provided in the metering chamber 612. The tail end of the actuator rod 642 contacts the resilient ball 634 of the outlet 630 valve. The shaft of the actuator rod 642 is housed within torque tube 652 and a handle 656 is provided to the head of the actuator rod 642.

Actuation of the valve of FIG. 7 is achievable by rotating the actuator rod 642 such that its tail end physically dislodges the resilient ball 634 from its seat 622. The actuator rod 642 is rotated by use of the handle 656 at its head. The handle 656 may be coupled to any suitable drive means including mechanical and electrical drive means (not shown).

FIGS. 8a to 8d show various forms of poppet valve suitable for use in accord with the invention. These employ valve poppets having different forms. These alternative valve poppets may be used in the metering valves of FIGS. 1 to 6 or the poppet valve actuation mechanism of FIG. 7 instead of the ball valve poppets shown therein.

Figure 8A:
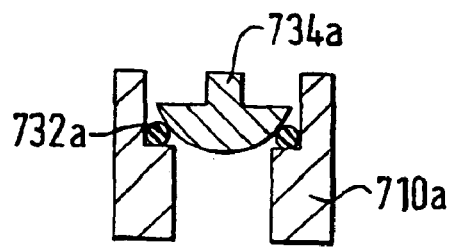
Figure 8B:
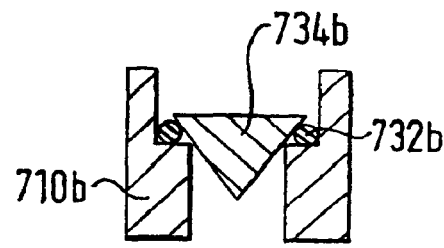
Figure 8C:
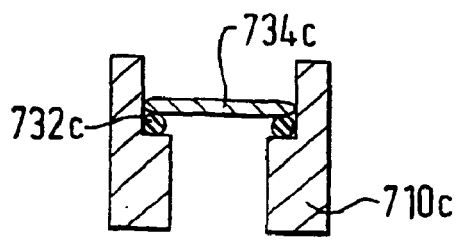
Figure 8D:
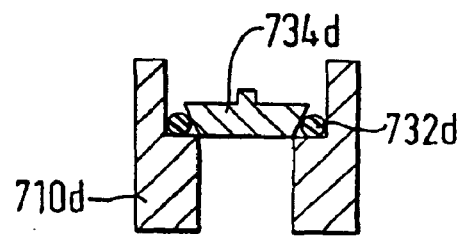

In more detail, FIGS. 8a to 8d show a valve body 710a–d supporting a valve 1 seat 732a–d and a valve poppet 734a–d which sits on valve seat 732a–d. In FIG. 8a the valve poppet 734a is in the form of a mushroom. In FIG. 8b the valve poppet 734b is in the form of a cone. In FIG. 8c the valve poppet 734c is in the form of a disc. In FIG. 8d the valve poppet 734d is in the form of a plug.

FIG. 9 shows an aerosol metering valve herein in the rest position. The valve comprises a valve body 810 which defines a metering chamber 812 and a sampling chamber 814. The metering chamber has an inlet 820 permitting flow of aerosol from the sampling chamber 814 and an outlet 830 permitting dispensing of aerosol from the metering chamber 812. The inlet 820 is provided with valve means comprising a valve seat 822 and a valve poppet in the form of a first shaped magnet 824 which has a flexible seal 823 provided thereto. The seal 823 is biased away from the valve seat 822 by the repulsive action of toroidal magnet 850. The outlet 830 is also provided with valve means comprising a valve poppet in the form of a second shaped magnet 834 having a flexible seal 833 biased into contact with a valve seat 832 by the attractive action of toroidal magnet 850. Both shaped magnets 824, 834 are chamfered to provide flow passageways therethrough.

Actuation of the metering valve of FIG. 9 is achievable by movement of the toroidal magnet 850 downwards which removes the repulsive force from the first shaped magnet 824 which may therefore contact the valve seat 822 closing the inlet 820. Simultaneously, the toroidal magnet 850 attracts the second shaped magnet 834 which moves off its seat 832 thereby opening the outlet 830. The toroidal magnet 850 may in turn be coupled to a mechanical trigger such as a lever mechanism (not shown).

FIG. 10 shows an aerosol metering valve herein. The metering valve comprises a valve body 910 which defines a metering chamber 912 and a sampling chamber 914. The sampling chamber 914 is funnel-shaped to encourage ready flow of aerosol from the container to the metering chamber 912. The metering chamber 912 has an inlet 920 permitting flow of aerosol from the sampling chamber 914 and an outlet 930 permitting dispensing of aerosol from the metering chamber 912. The inlet 920 is provided with valve means comprising a valve seat 922 and a valve poppet in the form of a resilient ball 924. The ball 924 is biased towards the valve seat 922 by the action of spring 926. The outlet 930 is also provided with valve means comprising a valve poppet in the form of a resilient ball 934 biased into contact with a valve seat 932 by action of spring 936. The valve body 910 is provided with fixing screws 905, 907 for fixing the valve to an aerosol container 903 (shown in part only). Shaped pins 940, 942 sit within and on both sides of access holes 916, 918 provided in the sampling chamber 914 and metering chamber 912 respectively. It may be seen that the tail end of each of the shaped pins 940, 942 contacts the resilient balls 924, 934 of the inlet 920 and outlet 930 valves respectively. It may also be seen that each of the pins 940, 942 is biased to a rest position by spring 944, 946 away from the respective resilient ball 924, 934. The outer heads of the transfer pins 941, 943 are shaped for impact. A suitable impactor (not shown) might for example, comprise an impacting arm as shown in FIG. 6 which may itself be connected to a breath-actuable vane.

Actuation of the metering valve of FIG. 10 is achievable by impacting the heads 941, 943 of the shaped pins 940, 942 to physically dislodge the resilient balls 924, 934 from their respective seats 922, 932. The action of the springs 944, 946 will return each pin to the rest position on removal of the impacting force. In a typical operation the inlet 920 valve will first be opened to allow metered flow of aerosol into the metering chamber 912. The outlet 930 valve is then opened to allow for dispensing of the aerosol. The impactor may be configured to allow for impaction of one of the shaped pins 940, 942, and hence opening of only one of the inlet 920 or outlet 930 valves, at a time.

FIG. 11 shows an aerosol metering valve herein. The metering valve comprises a valve body 1010 which defines a metering chamber 1012 and a sampling chamber 1014. The metering chamber 1012 has an inlet 1020 permitting flow of aerosol from the sampling chamber 1014 and an outlet 1030 permitting dispensing of aerosol from the metering chamber 1012. The inlet 1020 is provided with valve means comprising a valve seat 1022 and a valve poppet in the form of a cone 1024. The cone 1024 is biased towards the valve seat 1022 by the action of spring 1026 (rest position). The outlet 1030 is also provided with valve means comprising a valve poppet in the form of a cone 1034 biased into contact with a valve seat 1032 by action of spring 1036 (rest position). Shaped actuator pins 1040, 1042 sit within and on both sides of access passages 1016, 1018 provided in the valve body 1010. It may be seen that the tail end of each of the actuator pins 1040, 1042 connects with the cone poppets 1024, 1034 of the inlet 1020 and outlet 1030 valves respectively. It may also be seen that the tail end each of the pins 1040, 1042 is provided with protective bellow seals 1046, 1048 which provide a seal between the cone poppets 1024, 1034 and the actuator pins 1040, 1042. The outer heads of the transfer pins 1041, 1043 are shaped for impact. A suitable impactor (not shown) might for example, comprise an impacting arm as shown in FIG. 6 which may itself be connected to a breath-actuable vane.

Actuation of the metering valve of FIG. 11 is achievable by impacting the heads 1041, 1043 of the actuator pins 1040, 1042 to physically dislodge the cone poppets 1024, 1034 from their respective seats 1022, 1032. The action of the springs 1026, 1036 will return each pin 1040, 1042 to the rest position on removal of the impacting force. In a typical operation the inlet 1020 valve will first be opened to allow metered flow of aerosol into the metering chamber 1012. The outlet 1030 valve is then opened to allow for dispensing of the aerosol. The impactor may be configured to allow for impaction of one of the actuator pins 1040, 1042, and hence opening of only one of the inlet 1020 or outlet 1030 valves, at a time.

FIG. 12 shows an aerosol metering valve and aerosol container (in part) herein. The valve comprises a valve body 1110 which defines a metering chamber 1112 and a sampling chamber 1114. The sampling chamber 1114 has inlets 1116, 1117 permitting flow of aerosol from the aerosol container 1105. The metering chamber 1112 has an inlet 1120 permitting flow of aerosol from the sampling chamber 1114 and an outlet 1130 permitting dispensing of aerosol from the metering chamber 1112. The inlet 1120 is provided with valve means comprising a valve seat 1122 and a valve poppet in the form of a sliding piston 1124 with poppet head 1125. The poppet head 1125 of the sliding piston 1124 is biased towards the valve seat 1122 by the action of spring 1126. The outlet 1130 is also provided with valve means comprising a valve poppet in the form of a sliding piston 1134 with poppet head 1135 biased into contact with a valve seat 1132 by action of spring 1136. It may be seen that the bodies of sliding pistons 1124 and 1134, and their respective biasing springs 1126 and 1136, are respectively enclosed in hermetically sealed piston shafts 1128 and 1138. The ball-shaped 1125, 1135 poppet heads of the sliding pistons 1124, 1134 however, protrude from the piston shafts to contact the respective valve seats 1122, 1132. Shape memory alloy wires 1140; 1142 are fixed to the sliding pistons 1124, 1134 of the inlet 1120 and outlet 1130 valves respectively. The wires 1140, 1142 are also fixed to anchor points 1146, 1148 at the top of each respective piston shaft 1128, 1138. The wires 1140, 1142 are formed from a nickel/titanium alloy which contracts on heating, for example in response to electrical current flow. The wires 1140, 1142 are each connected to an electrical power source 1150, 1152.

Actuation of the metering valve of FIG. 12 is achievable by contraction of the shape memory alloy wires 1140, 1142 to move the sliding pistons 1124, 1134 within their respective shafts 1128, 1138 and hence to move the poppet heads 1125, 1135 from their respective seats 1122, 1132. Contraction of the wires 1140, 1142 is in turn achievable by the flow of electrical current through the wires 1140, 1142. In a typical operation the inlet 1120 valve will first be opened to allow metered flow of aerosol into the metering chamber 1112. The outlet 1130 valve is then opened to allow for dispensing of the aerosol.

FIG. 13 shows an aerosol metering valve herein which is a variation of the metering valve of FIG. 9. The valve comprises a valve body 1210 which defines a metering chamber 1212 and a sampling chamber 1214. The valve body 1210 is provided with fixing holes 1205, 1207 for screw-fixing the valve to an aerosol container (not shown). The metering chamber has an inlet 1220 permitting flow of aerosol from the sampling chamber 1214 and an outlet 1230 permitting dispensing of aerosol from the metering chamber 1212. The inlet 1220 has a bore which is narrow for ease of aerosol flow, typically being approximately 2 mm in diameter. The inlet 1220 is provided with valve means comprising a valve seat 1222 and a valve poppet in the form of a first shaped magnet 1224 which has a flexible ball head 1223 provided thereto. As shown, the magnet 1224 is biased away from the valve seat 1222 by the repulsive action of toroidal magnet 1250. When so biased away from the valve seat 1222, the magnet 1224 may move to position 1224*a* in which it abuts inclined surface 1209 at the mouth of the sampling chamber 1214 thereby permitting good aerosol flow to the inlet 1220 of the metering chamber 1212. The sampling chamber 1214 is also provided with slots 1215*a*, 1215*b* to further assist aerosol flow. The outlet 1230 has valve means comprising a valve poppet in the form of a second shaped magnet 1234 having a flexible ball head 1233 in contact with valve seat 1232. The metering chamber 1212 is provided with slots 1213*a*, 1213*b* to further assist aerosol flow. Both shaped magnets 1224, 1234 are chamfered to provide flow passageways therethrough.

Actuation of the metering valve of FIG. 13 is achievable by movement of the toroidal magnet 1250 downwards which removes the repulsive force from the first shaped magnet 1224 which may therefore contact the valve seat 1222 closing the inlet 1220. Simultaneously, the toroidal magnet 1250 attracts the second shaped magnet 1234 which moves off its seat 1232 thereby opening the outlet 1230. The toroidal magnet 1250 may in turn be coupled to a mechanical trigger such as a lever mechanism (not shown).

FIG. 14 shows an aerosol metering valve herein. The metering valve comprises a valve body 1310 which defines a metering chamber 1312 and a sampling chamber 1314. The valve body 1310 is provided with fixing screws 1305, 1307 for fixing the valve to an aerosol container (not shown).

The sampling chamber 1314 is funnel-shaped to encourage ready flow of aerosol from the container to the metering chamber 1312. The metering chamber 1312 has an inlet 1320 permitting flow of aerosol from the sampling chamber 1314 and an outlet 1330 permitting dispensing of aerosol from the metering chamber 1312. The inlet 1320 is provided with valve means comprising a valve seat 1322 in the form of a rubber o-ring and a valve poppet in the form of a resilient ball 1324. The outlet 1330 is also provided with valve means comprising a valve poppet in the form of a resilient ball 1334 contacting valve seat 1332. Actuator rods 1340, 1350 are snugly received by cavities in the resilient balls 1324, 1334 of the respective inlet and outlet valve poppets. The actuator rods 1340, 1350 also thread through resilient ball seals 1342, 1352 which sit within o-rings 1344, 1354 to form pivot seals. It may be appreciated that the ball poppets 1324, 1334 are movable by a pivoting (i.e. seesaw) movement of their respective actuator rods 1340, 1350 within the respective pivot seals. The ends 1346, 1356 of the actuator rods 1340, 1350 are biased by the action of torsion springs 1348, 1358 which act on the rods 1340, 1350 such that the poppet seals 1324, 1334 are biased to the closed position. The springs 1348, 1358 are attached to arms 1360, 1362 which protrude from the upper part of the valve body 1310. Stops 1364, 1366 are provided to prevent excessive movement of the actuator rods 1340, 1350 in the vertical (i.e. up/down) direction. The actuator rods 1340, 1350 may be connected to suitable breath-actuable vanes (not shown) to enable breath-actuation thereof.

Actuation of the metering valve of FIG. 14 is achievable by pivoting the actuator rods 1340, 1350 to dislodge the resilient balls 1324, 1334 from their respective seats 1322, 1332. The action of the springs 1348, 1358 will return each rod 1340, 1350 and associated ball poppet 1324, 1334 to the rest position on removal of the pivoting force. In a typical operation the inlet 1320 valve will first be opened to allow metered flow of aerosol into the metering chamber 1312. The outlet 1330 valve is then opened to allow for dispensing of the aerosol. The valve operation will typically be configured to allow for pivoting of one of the actuator rods 1340, 1350 and hence opening of only one of the inlet 1320 or outlet 1330 valves, at a time.

FIG. 15 shows a schematic representation of an inhalation device herein. The device comprises a housing 1460 including a mouthpiece 1462 and shaped for receipt of an aerosol container 1470. The aerosol container 1470 has a metering valve 1472 which may be any metering valve described herein. Within the aerosol container 1470 is provided stirrer 1471 for assisting in the agitation of the aerosol contents thereof prior to dispensing. The metering valve 1472 has a valve stem 1474 including a valve nozzle 1476 for dispensing aerosol 1478 therefrom. The metering valve 1472 connects with valve driver system 1480 which may comprise any of the valve driver or trigger elements described herein. The valve driver system 1480 in turn communicates with breath sensor system 1490 which may comprise any breath sensing mechanism described herein. Dose counter 1492 is provided to count the number of actuations of the valve 1472 and may be connected to a display (not shown) to display doses dispensed or doses remaining in the container 1470.

It may be appreciated that any of the parts of the metering valve which contact the medicament suspension may be coated with materials such as fluoropolymer materials which reduce the tendency of medicament to adhere thereto. Suitable fluoropolymers include polytetrafluoroethylene (PTFE) and fluoroethylene propylene (FEP). Any movable parts may also have coatings applied thereto which enhance their desired movement characteristics. Frictional coatings may therefore be applied to enhance frictional contact and lubricants used to reduce frictional contact as necessary.

The aerosol container and valve of the invention is suitable for dispensing medicament, particularly for the treatment of respiratory disorders such as asthma and chronic obstructive pulmonary disease (COPD).

Appropriate medicaments may thus be selected from, for example, analgesics, e.g., codeine, dihydromorphine, ergotamine, fentanyl or morphine; anginal preparations, e.g., diltiazem: antiallergics, e.g., cromoglycate, ketotifen or nedocromil; antiinfectives e.g., cephalosporins, penicillins, streptomycin, sulphonamides, tetracydines and pentamidine; antihistamines, e.g., methapyrilene; anti-inflammatories, e.g., beclomethasone dipropionate, fluticasone propionate, flunisolide, budesonide, rofleponide, mometasone furoate or triamcinolone acetonide; antitussives, e.g., noscapine; bronchodilators, e.g., albuterol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol, or (-)-4-amino-3,5-dichloro-α[[[6[2-(2-pyridinyl)ethoxy]hexyl]methyl] benzenemethanol; diuretics, e.g., amiloride; antcholinergics, e.g., ipratropium, tiotropium, atropine or oxitropium; hormones, e.g., cortisone, hydrocortisone or prednisofone; xanthines, e.g., aminophylline, choline theophyllinate, lysine theophyllinate or theophylline; therapeutic proteins and peptides, e.g., insulin or glucagon. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Preferred medicaments are selected from albuterol, salmeterol, fluticasone propionate and beclomethasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) in combination with an antiinflammatory steroid such as a beclomethasone ester (e.g., the dipropionate) or a fluticasone ester (e.g., the propionate).

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

What is claimed is:

1. A metering valve comprising:
   a valve body defining a metering chamber having an inlet and an outlet;
   an inlet valve adapted to be reversibly actuable from an open to a closed position located at the inlet;
   an outlet valve adapted to be reversibly actuable from a dispensing to a non-dispensing position located at the outlet, wherein said outlet valve includes an outlet valve seat adapted to be in biasable contact with an outlet valve poppet; and a magnetic actuating mechanism which is actuable to move the outlet valve poppet out of contact with the outlet valve seat.

2. The metering valve according to claim 1, wherein said inlet valve includes an inlet valve seat adapted to be in biasable contact with an inlet valve poppet.

3. The metering valve according to claim 2, wherein the inlet and/or outlet valve poppet includes an incompressible material, and wherein the inlet and/or outlet valve seat includes a compressible material.

4. The metering valve according to claim 2, wherein the inlet and/or outlet valve poppet includes a compressible material, and wherein the inlet and/or outlet valve seat includes an incompressible material.

5. The metering valve according to claim 2, wherein the inlet valve poppet is in the form of a ball, a mushroom, a cone, a disc or a plug.

6. An aerosol container comprising a metering valve according to claim 5.

7. The metering valve according to claim 2, wherein the magnetic actuating mechanism is further actuable to move the inlet valve poppet out of contact with the inlet valve seat.

8. The metering valve according to claim 7, wherein the magnetic actuating mechanism comprises a magnetically actuable inlet mover adapted to move the inlet valve poppet out of contact with the inlet valve seat.

9. An aerosol container comprising a metering valve according to claim 8.

10. The metering valve according to claim 7, wherein the magnetically actuable inlet valve mover includes a magnetic material or a magnetically inductive material.

11. An aerosol container comprising a metering valve according to claim 10.

12. The metering valve according to claim 7, wherein the inlet valve mover moves the inlet valve poppet out of contact with the inlet valve seat upon movement of the inlet valve mover from a first position to a second position, and wherein the magnetic actuating mechanism has an actuator element which is adapted to magnetically interact with the inlet valve mover to move it between the first and second positions.

13. An aerosol container comprising a metering valve according to claim 12.

14. The metering valve according to claim 7, wherein the magnetic actuating mechanism on actuation thereof magnetically interacts with the inlet valve poppet to cause said movement thereof.

15. An aerosol container comprising a metering valve according to claim 14.

16. The metering valve according to claim 7, wherein the magnetic actuating mechanism has a magnet element which is movable from a first position, in which the magnet element magnetically interacts with the outlet valve poppet to move the outlet valve poppet off the outlet valve seat, to a second position, in which the magnet element magnetically interacts with the inlet valve poppet to move the inlet valve poppet off the inlet valve seat.

17. The metering valve according to claim 16 constructed and arranged such that when the outlet valve poppet is out of contact with the outlet valve seat, the inlet valve poppet is always in contact with the inlet valve seat.

18. An aerosol container comprising a metering valve according to claim 17.

19. An aerosol container comprising a metering valve according to claim 16.

20. The metering valve according to claim 7 constructed and arranged such that when the outlet valve poppet is out of contact with the outlet valve seat, the inlet valve poppet is always in contact with the inlet valve seat.

21. An aerosol container comprising a metering valve according to claim 20.

22. An aerosol container comprising a metering valve according to claim 7.

23. An aerosol container comprising a metering valve according to claim 2.

24. The metering valve according to claim 1, wherein the inlet valve is in the closed position and the outlet valve is in the non-dispensing position when the metering valve is at rest.

25. The metering valve according to claim 1, wherein the inlet valve and the outlet valve are adapted to be independently operable.

26. The metering valve according to claim 1, wherein the outlet valve poppet is in the form of a ball, a mushroom, a cone, a disc or a plug.

27. An aerosol container comprising a metering valve according to claim 26.

28. The metering valve according to claim 1, wherein said valve body additionally defines a sampling chamber, and wherein the inlet is adapted to permit flow from the sampling chamber to the metering chamber.

29. The metering valve according to claim 28, wherein the metering chamber is adapted to have a fixed volume.

30. An aerosol container comprising a metering valve according to claim 29.

31. The metering valve according to claim 28, wherein the metering chamber is adapted to have a variable metering volume.

32. An aerosol container comprising a metering valve according to claim 31.

33. An aerosol container comprising a metering valve according to claim 28.

34. The metering valve according to claim 1, wherein the magnetic actuating mechanism comprises a magnetically actuable outlet mover adapted to move the outlet valve poppet out of contact with the outlet valve seat.

35. The metering valve according to claim 34, wherein the magnetically actuable outlet valve mover includes a magnetic material or a magnetically inductive material.

36. An aerosol container comprising a metering valve according to claim 35.

37. The metering valve according to claim 34, wherein the outlet valve mover moves the outlet valve poppet out of contact with the outlet valve seat upon movement of the outlet valve mover from a first position to a second position, and wherein the magnetic actuating mechanism has an actuator element which is adapted to magnetically interact with the outlet valve mover to move it between the first and second positions.

38. An aerosol container comprising a metering valve according to claim 37.

39. An aerosol container comprising a metering valve according to claim 24.

40. The metering valve according to claim 1, wherein the magnetic actuating mechanism on actuation thereof magnetically interacts with the outlet valve poppet to cause said movement thereof.

41. An aerosol container comprising a metering valve according to claim 40.

42. An aerosol container comprising a metering valve according to claim 1.

43. An aerosol container according to claim 42, wherein the valve body of the metering valve is not movable relative to the container.

44. An aerosol container according to claim 42, wherein the container contains a suspension of a medicament in a propellant.

45. An aerosol container according to claim 44, wherein said propellant comprises liquefied HFA-134a, HFA-227, or carbon dioxide.

46. An aerosol container according to claim 44, wherein the medicament is selected from the group consisting of albuterol, salmeterol, fluticasone propionate, beclomethasone dipropionate, salts or solvates thereof and any mixtures thereof.

47. An aerosol container according to claim 42, wherein the container contains a compressed gas.

48. An aerosol container according to claim 47, wherein the container contains compressed air.

49. An inhalation device for dispensing medicament to a patient comprising:
   a housing;
   an aerosol container, locatable within said housing, said aerosol container comprising a metering valve that comprises
      a valve body defining a metering chamber having an inlet and an outlet;
      an inlet valve adapted to be reversibly actuable from an open to a closed position located at the inlet;
      an outlet valve adapted to be reversibly actuable from a dispensing to a non-dispensing position located at the outlet, wherein said outlet valve includes an outlet valve seat adapted to be in biasable contact with an outlet valve poppet; and
      a magnetic actuating mechanism which is actuable to move the outlet valve poppet out of contact with the outlet valve seat; and
   an outlet valve trigger for triggering the movement of the outlet valve poppet out of contact with the outlet valve seat.

50. An inhalation device according to claim 49, wherein the outlet valve trigger is triggerable in response to the breath of a patient.

51. An inhalation device according to claim 50, wherein the outlet valve trigger is triggerable in response to the inward breath of a patient.

52. An inhalation device according to claim 50, wherein the outlet valve trigger is triggerable at a trigger point which is coupled to the end of the exhalation part of a patient's breath cycle.

53. An inhalation device according to claim 50, wherein the outlet valve trigger communicates with a sensor which senses the breath of a patient.

54. An inhalation device according to claim 53, wherein said sensor comprises a breath-movable element which is movable in response to the breath of a patient.

55. An inhalation device according to claim 54, wherein said breath-movable element is selected from the group consisting of a vane, a sail, a piston and an impeller.

56. An inhalation device according to claim 53, wherein said sensor comprises a pressure sensor for sensing the pressure profile associated with the breath of a patient.

57. An inhalation device according to claim 53, wherein said sensor comprises an airflow sensor for sensing the airflow profile associated with the breath of a patient.

58. An inhalation device according to claim 53, wherein said sensor comprises a temperature sensor for sensing the temperature profile associated with the breath of a patient.

59. An inhalation device according to claim 53, wherein said sensor comprises a moisture sensor for sensing the moisture profile associated with the breath of a patient.

60. An inhalation device according to claim 53, wherein said sensor comprises a gas sensor for sensing the oxygen or carbon dioxide profile associated with the breath of a patient.

61. An inhalation device according to claim 53, wherein said sensor comprises a piezoelectric or piezoresistive element.

62. An inhalation device according to claim 49, wherein the inlet valve further comprises an inlet valve seat and an inlet valve poppet in biasable contact therewith.

63. An inhalation device according to claim 62, further comprising an inlet valve trigger for triggering the movement of the inlet valve poppet out of contact with the inlet valve seat.

64. An inhalation device according to claim 63, wherein the outlet valve trigger and the inlet valve triggers are both magnetic triggers.

65. An inhalation device according to claim 64, wherein the outlet valve trigger interacts magnetically with an outlet shuttle contacting the outlet valve poppet and/or the inlet valve trigger interacts magnetically with an inlet shuttle contacting the inlet valve poppet.

66. An inhalation device according to claim 65, wherein the outlet shuttle comprises a magnetic material.

67. An inhalation device according to claim 65, wherein the outlet shuttle comprises a material which is magnetically inductive and the outlet valve trigger comprises an inductive element capable of inducing magnetism therein and/or the inlet shuttle comprises a material which is magnetically inductive and the inlet valve trigger comprises an inductive element capable of inducing magnetism therein.

\* \* \* \* \*